(12) United States Patent
Kim et al.

(10) Patent No.: US 9,782,086 B2
(45) Date of Patent: Oct. 10, 2017

(54) APPARATUS AND METHOD OF MEASURING BLOOD PRESSURE

(71) Applicant: Samsung Electronics Co., Ltd., Suwon-si, Gyeonggi-do (KR)

(72) Inventors: Youn-ho Kim, Yongin-si (KR); Kun-soo Shin, Yongin-si (KR); Sang-kon Bae, Yongin-si (KR); Seok-chan Kim, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 41 days.

(21) Appl. No.: 14/254,238

(22) Filed: Apr. 16, 2014

(65) Prior Publication Data

US 2014/0228694 A1    Aug. 14, 2014

Related U.S. Application Data

(63) Continuation of application No. 12/612,889, filed on Nov. 5, 2009, now abandoned.

(30) Foreign Application Priority Data

Nov. 6, 2008  (KR) .................. 10-2008-0110005

(51) Int. Cl.
*A61B 5/0225* (2006.01)
*A61B 5/021* (2006.01)
*A61B 5/022* (2006.01)

(52) U.S. Cl.
CPC ........ *A61B 5/02141* (2013.01); *A61B 5/0225* (2013.01); *A61B 5/02108* (2013.01); *A61B 5/02116* (2013.01); *A61B 5/02225* (2013.01)

(58) Field of Classification Search
CPC . A61B 5/02225; A61B 5/022; A61B 5/02116; A61B 5/021
USPC .................................................. 600/490–499
See application file for complete search history.

(56) References Cited

U.S. PATENT DOCUMENTS 4,271,843 A  *  6/1981  Flynn ........................... 600/494
4,427,013 A  *  1/1984  Nunn et al. ................... 600/494
5,255,686 A     10/1993  Takeda et al.
5,368,039 A  *  11/1994  Moses ........................... 600/494

(Continued)

FOREIGN PATENT DOCUMENTS

JP    05-146414    6/1993
JP    07-124130    5/1995

(Continued)

*Primary Examiner* — Patricia Mallari
*Assistant Examiner* — Michael Catina
(74) *Attorney, Agent, or Firm* — Cantor Colburn LLP (57) ABSTRACT

Provided is a blood pressure measuring apparatus including: a pressurizing unit applying pressure to a blood vessel according to a first condition or a second condition; a pressure sensor sensing a sphygmus wave and a pressure of the blood vessel from the blood vessel under the first condition or the second condition; a standard blood pressure calculating unit for calculating a systolic standard blood pressure and a diastolic standard blood pressure; a continuous blood pressure calculating unit for calculating continuous blood pressure; and a repressurizing determining unit for determining whether pressure is applied to the blood vessel under the second condition during measuring of continuous blood pressure.

11 Claims, 7 Drawing Sheets

(56) References Cited

U.S. PATENT DOCUMENTS

| | | | | |
|---|---|---|---|---|
| 5,848,970 | A * | 12/1998 | Voss et al. | 600/485 |
| 6,471,655 | B1 * | 10/2002 | Baura | 600/485 |
| 6,932,772 | B2 * | 8/2005 | Kan | A61B 5/02116 600/485 |
| 2002/0169380 | A1 * | 11/2002 | Hasegawa et al. | 600/485 |
| 2003/0236465 | A1 * | 12/2003 | Narimatsu et al. | 600/490 |
| 2004/0059234 | A1 * | 3/2004 | Martin et al. | 600/500 |
| 2005/0148885 | A1 * | 7/2005 | Tweed et al. | 600/490 |
| 2006/0116588 | A1 * | 6/2006 | Archibald et al. | 600/494 |

FOREIGN PATENT DOCUMENTS

| | | |
|---|---|---|
| JP | 07-236616 | 9/1995 |
| JP | 11-244247 | 9/1999 |
| KR | 1020060111391 A | 10/2006 |

\* cited by examiner

APPARATUS AND METHOD OF MEASURING BLOOD PRESSURE

CROSS-REFERENCE TO RELATED APPLICATIONS

This application is a continuation of U.S. patent application Ser. No. 12/612,889, filed Nov. 5, 2009, which claims priority to Korean Patent Application No. 10-2008-0110005, filed on Nov. 6, 2008 and all the benefits accruing therefrom under 35 U.S.C. §119. The contents of each of these applications, in their entirety, are herein incorporated by reference.

BACKGROUND

1. Field

Disclosed herein is an apparatus and a method of continuously measuring blood pressure of an examinee using a tonometric method.

2. Description of the Related Art

Various types of blood pressure measuring apparatuses have been developed in response to increasing public concerns about health. Examples of blood pressure measuring methods include a Korotkoff sound method, an oscillometric blood pressure measuring method, a tonometric blood pressure measuring method, and the like. The Korotkoff sound method is a typical pressure measuring method, which measures the systolic pressure at which the pulse sound of a living being is first heard and the diastolic pressure at which the pulse sound is barely audible during a decompression process. For the Korotkoff sound method a pressure is applied to a part of a body where arterial blood flows and the blood flow is blocked and then the applied pressure is reduced. As the pressure is reduced, a first pressure is measured when a sound of the pulse of a living being is heard first as a systolic pressure and a last pressure is measured at which the sound of the pulse a living being disappears as a diastolic pressure.

The oscillometric method and the tonometric method are used for digital blood pressure measuring apparatuses. The oscillometric method detects a sphygmus wave, which occurs in a decompression process after sufficiently compressing a body part through which arterial blood flows so as to block arterial blood flow in a manner that is similar to the Korotkoff sounds method, or in a compression process in which the body part is compressed at a predetermined compression speed. A pressure at which the amplitude of the sphygmus wave is at a specific level may be measured as a systolic pressure or as a diastolic pressure. Alternatively, a pressure at which the amplitude of the sphygmus wave changes suddenly may be measured as a systolic pressure or as a diastolic pressure.

During the decompressing process at a predetermined compression speed after compressing the body part, a systolic pressure is measured prior to a point of time at which the amplitude of the sphygmus wave is at a maximum, and a diastolic pressure is measured after a point of time at which the amplitude of the sphygmus wave is at the maximum. On the other hand, during the compression speed, a systolic pressure is measured after the point of time at which the amplitude of the sphygmus wave is at the maximum, and a diastolic pressure is measured prior to the point of time at which the amplitude of the sphygmus wave is at the maximum.

The tomometric method includes applying a certain pressure to a body part so that the arterial blood flow is not completely blocked and continuously measuring the blood pressure using the amplitude and form of a sphygmus wave that is generated by compressing the body part. Since the tonometric method requires continuously applying pressure for a long time, it may be burdensome to the examinee. Meanwhile, when the measured blood pressure abruptly changes during the measuring of the blood pressure by the tonometric method, it should be determined whether this change is caused by the actual change in the blood pressure of the examinee or by the inaccuracy of applying pressure the body part.

SUMMARY

Disclosed herein is an apparatus and a method of measuring blood pressure with reduced inconvenience caused due to applying pressure to a body part when measuring continuous blood pressure.

Disclosed herein is an apparatus and a method of measuring blood pressure with reduced error in measured values caused due to inappropriate application of pressure to a body part when measuring continuous blood pressure.

Additional aspects will be set forth in part in the description which follows and, in part, will be apparent from the description.

To achieve the above and/or other aspects, one or more embodiments may include a blood measuring apparatus including a pressurizing unit for applying pressure to a blood vessel of an examinee according to a first condition or a second condition; a pressure sensor for sensing a sphygmus wave and a pressure of the blood vessel under the first condition or the second condition; a standard blood pressure calculating unit for calculating a systolic standard blood pressure and a diastolic standard blood pressure of the examinee based on the sphygmus wave and the blood vessel pressure sensed by the pressure sensor under the first condition; a continuous blood pressure calculating unit for calculating continuous blood pressure of the examinee based on the sphygmus wave and the blood vessel pressure sensed by the pressure sensor under the second condition and based on the systolic standard blood pressure or the diastolic standard blood pressure; and a repressurizing determining unit for determining whether pressure applied to the blood vessel during measuring of continuous blood pressure deviates from the second condition, wherein when the repressurizing determining unit determines that pressure applied to the blood vessel of the examinee deviates from the second condition, the pressurizing unit applies pressure to the blood vessel of the examinee again under the second condition.

To achieve the above and/or other aspects, one or more embodiments may include a blood pressure measuring apparatus including: a pressurizing unit for applying pressure to a blood vessel of an examinee according to a first condition or a second condition; a pressure sensor for sensing a sphygmus wave and the pressure of the blood vessel under the first condition or the second condition; a standard blood pressure calculating unit for calculating a systolic standard blood pressure and a diastolic standard blood pressure of the examinee based on the sphygmus wave and the blood vessel pressure sensed by the pressure sensor under the first condition; an applied pressure determining unit for determining an applied pressure under a second condition for measuring continuous blood pressure; and a continuous blood pressure calculating unit for calculating continuous blood pressure of the examinee based on a sphygmus wave and the blood vessel pressure sensed by the pressure sensor while applying the determined applied pressure to the blood vessel under the second condition and based on the systolic standard blood pressure and the diastolic standard blood pressure.

To achieve the above and/or other aspects, one or more embodiments may include a method of measuring blood pressure, the method including: applying pressure to a blood vessel of an examinee under a first condition for measuring a standard blood pressure; calculating standard systolic and diastolic standard blood pressures of the examinee based on a sphygmus wave and the blood vessel pressure sensed while applying pressure to the blood vessel under the first condition; applying pressure to the blood vessel under a second condition for measuring continuous blood pressure; measuring continuous blood pressure of the examinee based on a sphygmus wave and the blood vessel pressure of the examinee sensed while applying pressure to the blood vessel under the second condition, and based on the systolic and diastolic standard blood pressures; determining whether to reapply pressure by determining whether pressure applied to the blood vessel of the examinee during the measuring of continuous blood pressure deviates from the second condition; and reapplying pressure to the blood vessel of the examinee under the second condition when it is determined that pressure applied to the blood vessel of the examinee during the meaning of continuous blood pressure deviates from the second condition.

To achieve the above and/or other aspects, one or more embodiments may include a method of measuring blood pressure, the method including: applying pressure to a blood vessel of an examinee under a first condition for measuring a standard blood pressure; calculating systolic and diastolic standard blood pressures of the examinee based on a sphygmus wave and the blood vessel pressure sensed while applying pressure to the blood vessel under the first condition determining a second condition for measuring continuous blood pressure such that an applied pressure under the second condition is a value less than the diastolic standard blood pressure applying the determined applied pressure to the blood vessel under the second condition; and measuring continuous blood pressure of the examinee based on a sphygmus wave and the blood vessel pressure of the examinee sensed while applying the determined applied pressure to the blood vessel under the second condition, and based on the systolic and diastolic standard blood pressures.

The first condition may be an increased pressure condition under which the pressure is increased at a uniform pressure variation rate to pressurize the blood vessel, or a reduced pressure condition under which pressure applied to the blood vessel is reduced at a uniform pressure variation rate after pressure is applied to the blood vessel to block the block vessel.

The second condition may be a fixed pressure condition under which a uniform pressure is applied to the blood vessel of the examinee without completely blocking the blood vessel.

In the determining whether to reapply pressure, if the difference between an amplitude of a baseline of the sphygmus wave sensed at a first time after starting the measurement of continuous blood pressure and an amplitude of a baseline of the sphygmus wave sensed at a second time that is later than the first time reaches at least a first criterion, and a ratio of a pulse amplitude of the sphygmus wave at the first time to a pulse amplitude of the sphygmus wave at the second time is less than or equal to a second criterion, it may be determined that pressure is not being applied to the blood vessel of the examinee under the second condition. The first criterion may be a value corresponding to a pressure difference of 5 mmHg, and the second criterion may be 80%.

The applied pressure under the second condition may be less than 80% of the diastolic standard blood pressure, and a pressure at which an inflection point of an envelope line occurs may be determined as the applied pressure under the second condition, wherein the envelope line is formed by connecting high peaks of the sphygmus wave sensed by the pressure sensor under the first condition.

BRIEF DESCRIPTION OF THE DRAWINGS

These and/or other aspects, advantages and features will become apparent by describing in further detail exemplary embodiments thereof with reference to the attached drawings, in which.

DETAILED DESCRIPTION

Aspects, advantages, and features of the present invention and methods of accomplishing the same may be understood more readily by reference to the following detailed description of preferred embodiments and the accompanying drawings. The present invention may, however, may be embodied in many different forms, and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the present invention.

Spatially relative terms, such as "below", "lower", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described in detail with reference to the accompanying drawings. However, the aspects, features, and advantages of the present invention are not restricted to the ones set forth herein. The above and other aspects, features and advantages of the present invention will become more apparent to one of ordinary skill in the art to which the present invention pertains by referencing a detailed description of the present invention given below.

Figure 1:
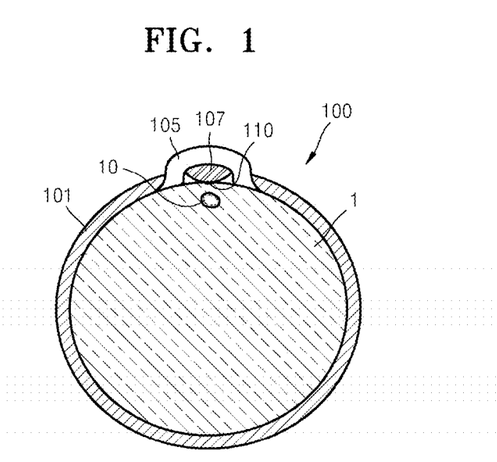
FIG. 1 is a schematic diagram showing a cross-sectional view illustrating an exemplary blood pressure measuring apparatus.

FIG. 1 is a schematic diagram showing a cross-sectional view illustrating an exemplary blood pressure measuring apparatus 100. It is noted that while the blood pressure measuring apparatus 100 is described herein in terms of a method and apparatus for monitoring arterial blood pressure suitable for use on the radial artery (i.e., wrist) of a human subject, the blood pressure measuring apparatus may also conceivably be embodied or adapted to monitor arterial blood pressure at other locations on the human body, as well as monitoring blood pressure on other warm-blooded species. All such adaptations and alternate embodiments are considered to fall within the scope of the claims appended hereto.

The blood pressure measuring apparatus 100 is worn on a wrist 1 through which a radial artery 10 passes so that a sphygmus wave and the pressure of a blood vessel can be easily sensed. The blood pressure measuring apparatus 100 includes a wrist band 101 that may be attached around the wrist 1 of the examinee and a blood pressure measuring block 105 for measuring the blood pressure. The blood pressure measuring block 105 includes a pressurizing unit for applying pressure to the radial artery 10 inside the wrist 1 of the examinee being subjected to measurement. The pressurizing unit includes a pressurizing member 107 that protrudes from the blood pressure measuring block 105 toward the wrist 1 and an actuator 108 (see FIG. 2) driving the pressurizing member 107 to protrude or contract. The pressurizing unit pressurizes the radial artery 10 under a first condition or a second condition. A pressure sensor 110 which senses a sphygmus wave and the pressure of the blood vessel from the radial artery 10 of the examinee is formed at an end of the pressurizing member 107 contacting the wrist 1.

Figure 2:
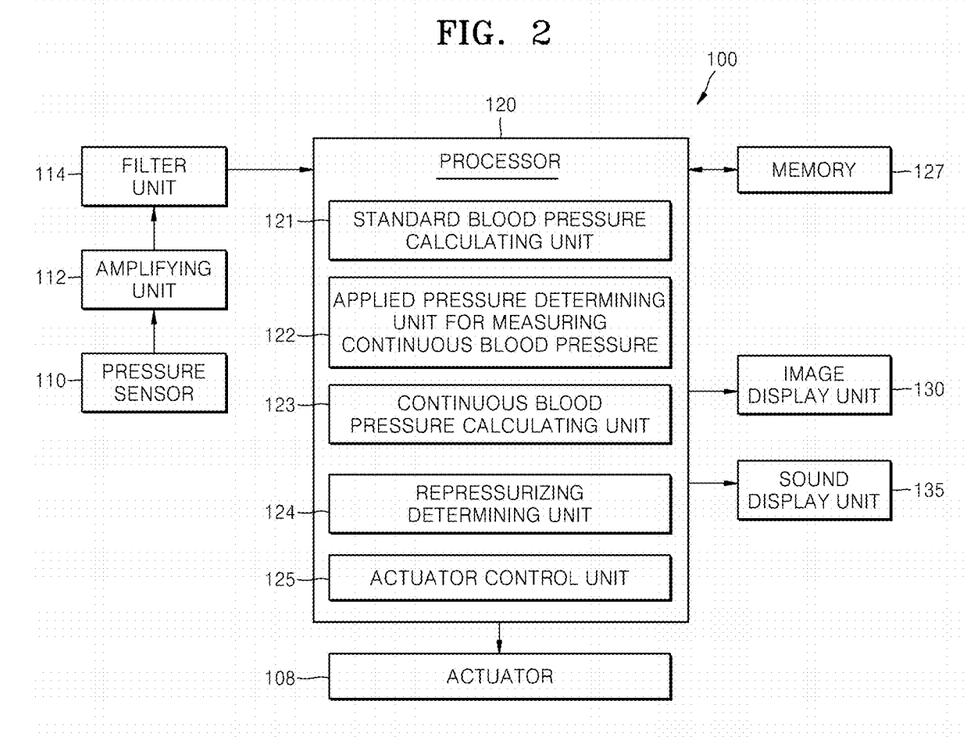
FIG. 2 is an exemplary block diagram illustrating a configuration of the blood pressure measuring apparatus of FIG. 1.

FIG. 2 is a block diagram illustrating an exemplary configuration of the blood pressure measuring apparatus 100 of FIG. 1.

Referring to FIG. 2, the blood pressure measuring apparatus 100 includes the pressure sensor 110, an amplifying unit 112 amplifying a signal generated in the pressure sensor 110, a filter unit 114 removing noise components from the amplified signal, a processor 120 conducting calculations using the filtered signal, and a memory 127 storing data and programs needed by the processor 120 to perform the calculations. The processor 120 includes a standard blood pressure calculating unit 121 that calculates systolic and diastolic standard blood pressures Psys and Pdia (refer to FIG. 3) of the examinee based on the sphygmus wave and the blood vessel pressure sensed by the pressure sensor 110 under the first condition, a continuous blood pressure calculating unit 123 that calculates continuous blood pressure of the examinee based on the sphygmus wave and the blood vessel pressure sensed by the pressure sensor 110 under the second condition and based on the systolic and diastolic standard blood pressures Psys and Pdia, a repressurizing determining unit 124 that determines whether pressure is applied to the radial artery 10 under the second condition or not during measuring of continuous blood pressure, and an actuator control unit 125 controlling a driving motion of the actuator 108. Also, the processor 120 further includes an applied pressure determining unit 122 for measuring continuous blood pressure, which determines the applied pressure under the second condition to be less than the diastolic standard blood pressure Pdia of the second condition.

Meanwhile, the blood pressure measuring apparatus 100 further includes an image display unit 130 visually displaying the measured blood pressure and a sound unit 135 audibly indicating the process of measuring blood pressure. The image display unit 130 may include a display panel, and the sound unit 135 may include a speaker.

Figure 3:
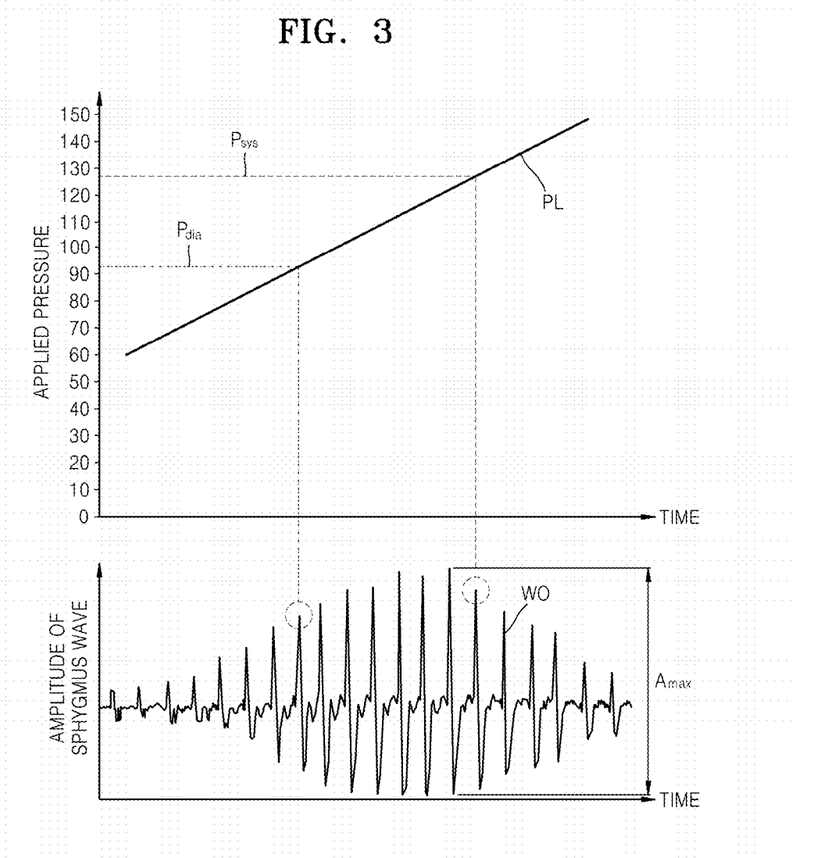
FIG. 3 is a graph showing a sphygmus wave that is detected when measuring systolic and diastolic standard blood pressures which are the standards for calculating continuous blood pressure.
Figure 4:
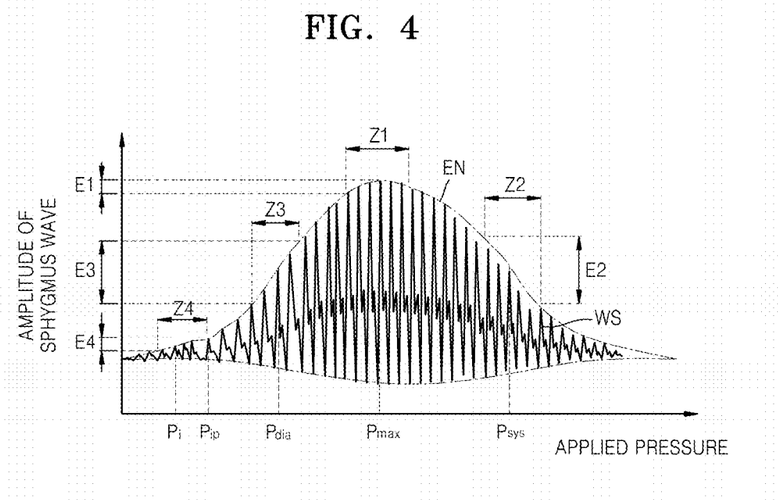
FIG. 4 is a graph illustrating a sphygmus wave which is the grounds for determining an applied pressure when measuring continuous blood pressure.
Figure 5:
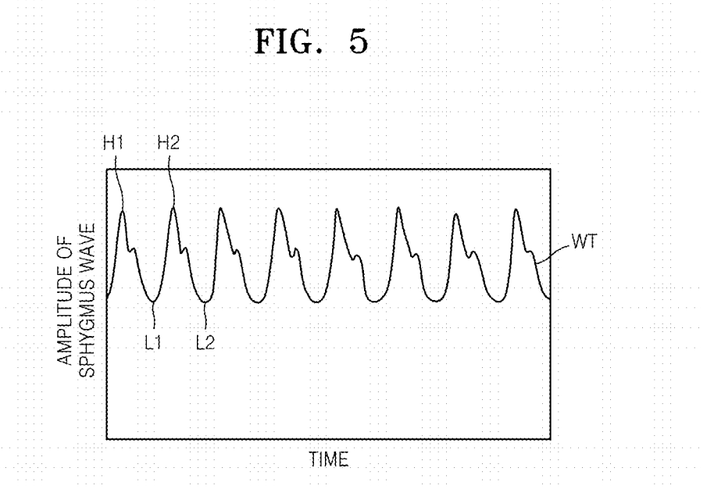
FIG. 5 is a graph illustrating a sphygmus wave detected at the beginning of measuring continuous blood pressure.
Figure 6:
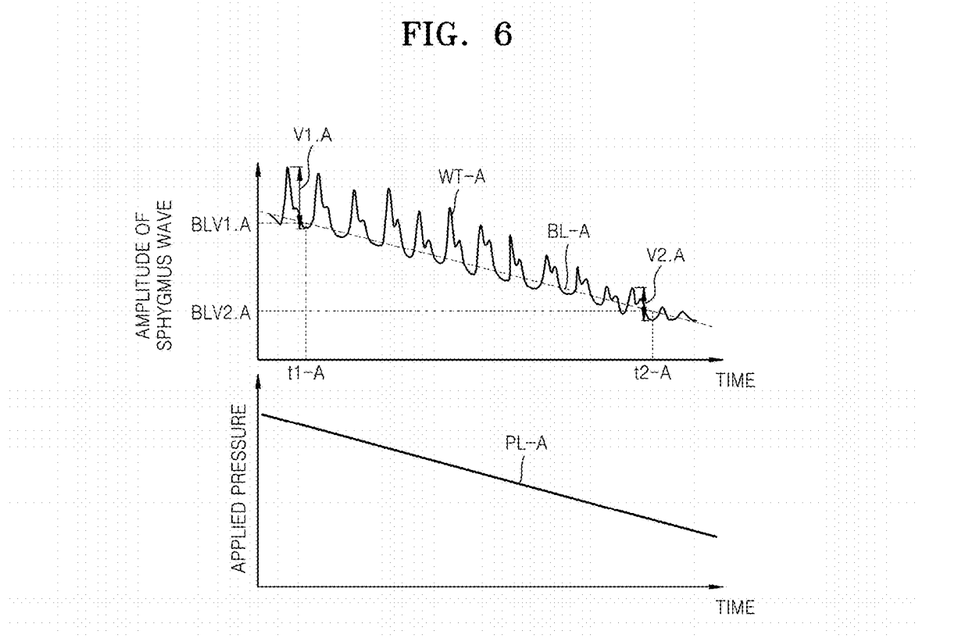
FIG. 6 is a graph illustrating an abnormal sphygmus wave that is detectable when measuring continuous blood pressure.
Figure 7:
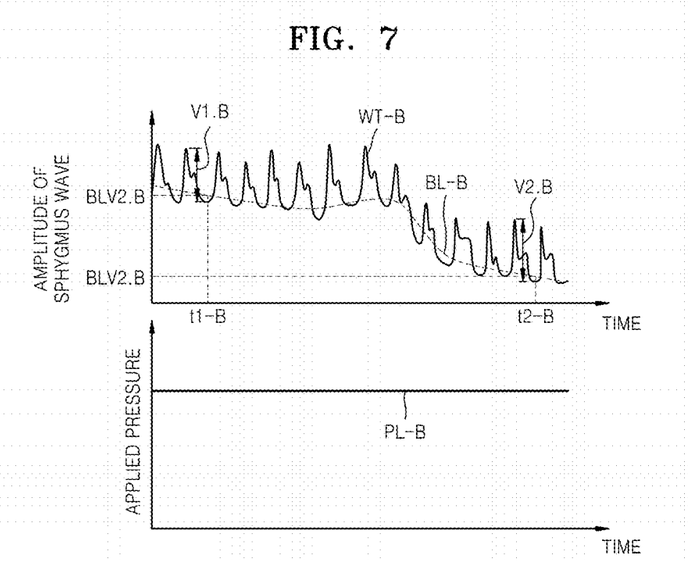
FIG. 7 is a graph illustrating an abnormal sphygmus wave that is detectable when measuring continuous blood pressure.

FIG. 3 is a graph showing a sphygmus wave detected when measuring systolic and diastolic standard blood pressures which are the standards for calculating continuous blood pressure. FIG. 4 is a graph illustrating a sphygmus wave which is the grounds for determining an applied pressure when measuring continuous blood pressure. FIG. 5 is a graph illustrating a sphygmus wave detected at the beginning of measuring continuous blood pressure according to an embodiment. FIG. 6 is a graph illustrating an abnormal sphygmus wave that is detectable when measuring continuous blood pressure according to an embodiment. FIG. 7 is a graph illustrating an abnormal sphygmus wave that is detectable when measuring continuous blood pressure, according to another embodiment. Hereinafter, elements of the blood pressure measuring apparatus 100 and their functions, and a method of measuring a blood pressure using the blood pressure measuring apparatus 100 will be described.

In one embodiment, the blood pressure measuring method includes applying pressure for measuring a standard blood pressure in which the pressurizing member 107 applies pressure to the radial artery 10 of the examinee under the first condition by driving the actuator 108, and measuring a standard blood pressure, in which the systolic and diastolic standard blood pressures Psys and Pdia (refer to FIG. 3) are calculated based on a sphygmus wave WO (see FIG. 3) and a pressure PL applied to the blood vessel (see FIG. 3) that are sensed when applying pressure for measuring a standard blood pressure as described above. The standard blood pressure is measured using an oscillometric method, and the measurement is conducted by the standard blood calculating unit 121. Line "PL" demonstrates the applied pressure using the pressurizing member 107 (refer to FIG. 3).

Figure 8:
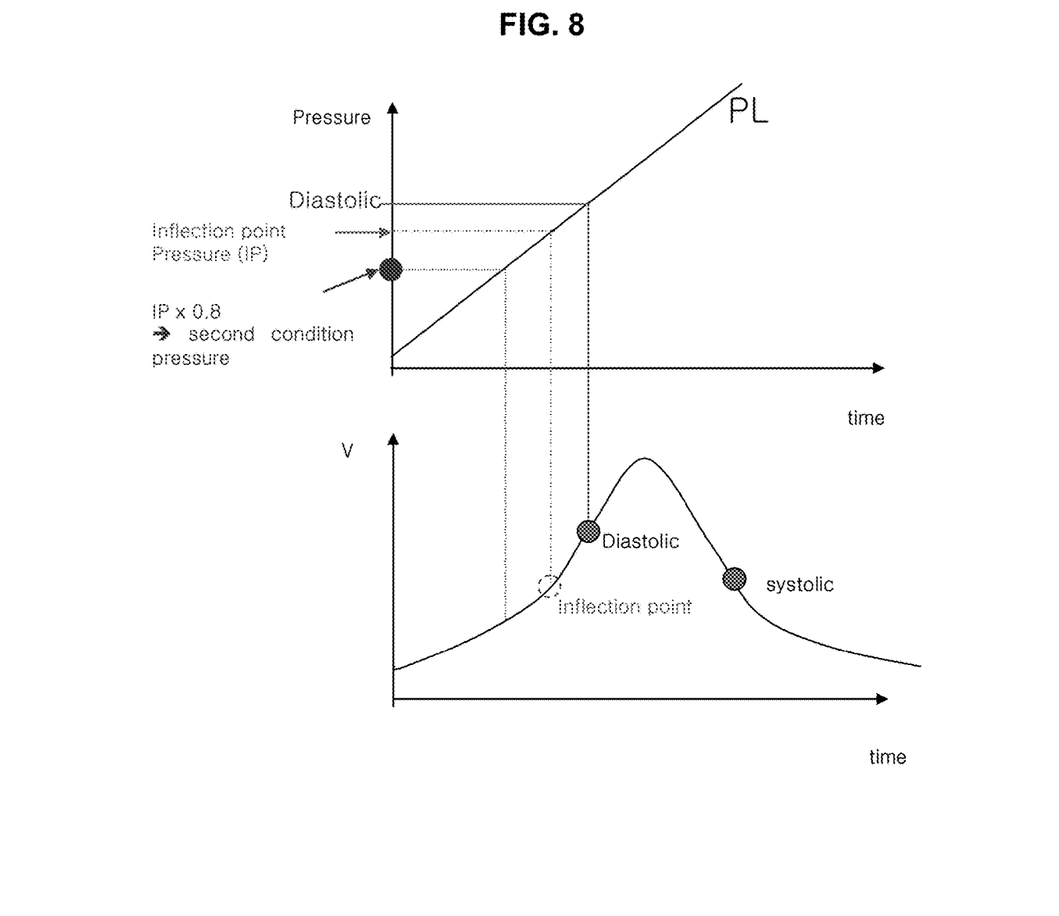
FIG. 8 provides a graph showing the envelope line of sphygmus wave that is detected when measuring systolic and diastolic standard blood pressures and a graph showing pressure protocol over time.

In one embodiment, the first condition refers to the period during which the pressure is applied to the radial artery at a certain rate. In FIG. 8, for example, the increasing pressure line PL represents pressure change during the first condition pressure protocol. Generally, the pressure is controlled to increase or decrease at a rate of less than 3 mmHg per 1 heartbeat. For convenience, it is assumed to be 3 mmHg/sec (60 beats/min).

Referring to FIG. 3, the first condition is an increased pressure condition under which the pressure is increased with a uniform pressure variation rate so as to apply pressure to the radial artery 10 by using the pressurizing member 107 (refer to FIG. 1) and the graph of the pressure may be as a line PL. For example, the inclination of the line PL may be 3 mmHg/sec. Here, the graph of the sphygmus wave of the examinee may be like a line marked with WO.

A pressure, which is detected by the pressure sensor 110 at a predetermined point after the amplitude of the sphygmus wave reaches a maximum Amax, is determined to be a systolic standard blood pressure Psys of the examinee, and a pressure, which is detected by the pressure sensor 110 before the maximum amplitude Amax, is determined as a diastolic standard blood pressure Pdia. Pressures at a point of time when the proportions of the pressures to the maximum amplitude Amax of the sphygmus wave are predetermined values may be determined as the systolic standard blood pressure Psys and the diastolic standard blood pressure Pdia, or pressures at a point of time point when the inclination of an envelope line of the sphygmus wave is abruptly changing may be determined as the systolic standard blood pressure Psys and the diastolic standard blood pressure Pdia. Meanwhile, the first condition for measuring a standard blood pressure is not limited to the increased pressure condition, but may also be a reduced pressure condition under which the pressure of the radial artery 10 of FIG. 1 is reduced at a predetermined pressure variation rate after the radial artery 10 is blocked by pressurizing.

In another embodiment, the blood pressure measuring method includes determining an applied pressure for measuring continuous blood pressure in which a pressurizing pressure of the second condition which is different from the first condition is determined, applying pressure to the radial artery 10 of the examinee for measuring continuous blood pressure in which the actuator 108 is driven such that the pressurizing member 107 applies pressure to the radial artery 10 under the second condition, and measuring continuous blood pressure in which continuous blood pressure of the examinee is calculated based on a sphygmus wave WT (refer to FIG. 5) sensed during the applying the pressure for measuring continuous blood pressure, and based on the systolic and diastolic standard blood pressures Psys and Pdia. The determining of the applied pressure for measuring continuous blood pressure is conducted using the applied pressure determining unit 122, and the measuring of continuous blood pressure is conducted using a tonometric method using the continuous blood pressure calculating unit 123. In the tonometric method, the second condition is a fixed pressure condition under which pressure is applied to the radial artery 10 without blocking the radial artery 10 completely.

When pressure is applied to the radial artery 10 under the increasing pressure condition with a uniform pressure variation rate, the applied pressure is increased in proportion with time, and thus the graph of a sphygmus wave according to the applied pressure may be shown as a line WS illustrated in FIG. 4. In FIG. 4, the high peaks of the sphygmus wave WS are connected to one another, and low peaks are connected to one another, and these connected lines are referred to as an envelope line EN. When the radial artery 10 is pressurized with an applied pressure with the maximum amplitude of the sphygmus wave, that is, a maximum pressure Pmax, the amplitude of the sphygmus wave sensed is relatively large. Also, in a range Z1 including the maximum pressure Pmax, a variation range E1 of the amplitude of the sphygmus wave within the envelope line EN is small even when the applied pressure changes within the range Z1.

The applied pressure range Z1 represents an error range of the maximum applied pressure Pmax, and the variation range E1 of the sphygmus wave is in proportion to the error possibility of the continuous blood pressure measurement corresponding to the applied pressure range Z1. For example, when the maximum pressure Pmax is set as the applied pressure of the second condition, the accuracy of measuring continuous blood pressure using a tonometric method can be improved in spite of the error in the applied pressure. However, this method may increase inconvenience or discomfort of the examinee because a certain pressure has to be continuously applied to the blood vessel for measuring continuous blood pressure.

On the other hand, when pressure is applied in a range Z2 including the systolic standard blood pressure or in a range Z3 including the diastolic standard blood pressure, variation ranges E2 or E3 in the sphygmus wave WS of the envelope line EN are relatively large when the applied pressure changes within the range Z2 or the range Z3. In other words, when the systolic standard blood pressure Psys or the diastolic pressure Pdia is set as the applied pressure of the second condition, the accuracy of measuring continuous blood pressure may decrease due to the error in the applied pressure.

Meanwhile, when pressure is applied in a range Z4 including a pressure Pi that is less than the diastolic standard blood pressure Pdia, a variation range E4 in the sphygmus wave WS of the envelope line EN is relatively small even when the applied pressure changes within the range Z4. That is, when the pressure Pi that is less than the diastolic standard blood pressure (Pdia) is determined as the applied pressure of the second condition, the accuracy of measuring continuous blood pressure can be improved in spite of the error in the applied pressure. Further, since a pressure lower than the diastolic standard blood pressure Pdia is applied to the radial artery 10, the inconvenience or discomfort of the examinee during the pressurizing for measuring continuous blood pressure can be greatly reduced. According to an embodiment, the pressure Pi of the second condition may be determined to be less than or equal to 80% of the diastolic standard blood pressure Pdia during the determining of the applied pressure for measuring continuous blood pressure. Obviously, the applied pressure Pi should always be greater than a pressure at which a sphygmus wave can be sensed using the pressure sensor 110.

Meanwhile, the applied pressure of the second condition is less than the diastolic standard blood pressure Pdia, and may be a pressure Pip at which an inflection point of the envelope line EN which is formed by connecting high peaks of the sphygmus wave WS sensed by the pressure sensor 110 under the first condition occurs. In one embodiment, the second condition pressure is defined as 80% of the pressure at which the slope of the pressure waveform envelope generated by connecting peaks of the pressure waveform is the greatest (inflection point) below the diastolic blood pressure (refer to the figure below). (FIG. 8) During the second condition pressure protocol, a uniform pressure that does not completely occlude the blood vessel is applied to the blood vessel.

Referring to FIG. 5, a tonometric sphygmus wave WT sensed by the pressure sensor 110 while the pressure is applied for measuring continuous blood pressure has a pattern with high peaks, for example, H1 and H2, and low peaks, for example, L1 and L2, being alternately repeated. Blood pressure at a moment of a first high peak H1 along this sphygmus wave WT is regarded as a systolic standard blood pressure Psys, and blood pressure at a moment of a first low peak L1 is regarded as a diastolic standard blood pressure Pdia. This is referred to as blood pressure calibration.

By applying an amplitude difference between the moment of the second high peak H2 and the high peak H1 to a regression equation for calculating tonometric blood pressure, the systolic pressure at the moment of the peak H2 can be obtained. A systolic pressure of a next high peak can also be obtained in the same manner as the systolic pressure at the moment of H2 is detected. Meanwhile, a diastolic pressure of the moment of a second low peak L2 can be obtained by applying an amplitude difference between the second low peak L2 and the low peak L1 to the regression equation for calculating tonometric blood pressure. Then, a diastolic pressure at a moment of subsequent low peaks can be obtained in the same manner as the diastolic pressure at the moment of the low peak L2 is detected. Calculating the blood pressures at the high peaks such as H1 and H2 and the low peaks L1 and L2 alternately and continuously in this way is the operation of measuring continuous blood pressure. Data of the calculated continuous blood pressure may be stored in the memory 127.

The blood pressure measuring method further includes determining whether to reapply pressure by determining whether pressure is applied to the radial artery 10 of the examinee under the second condition or not during the measuring of continuous blood pressure, and reapplying pressure to the radial artery 10 by driving the actuator 108 again so that the pressurizing member 107 reapplies pressure to the radial artery 10 under the second condition if it is determined that pressure is not being applied to the radial artery 10 under the second condition. The determining whether to reapply the pressure is conducted by the repressurizing determining unit 124, and the pressure is reapplied as the actuator control unit 125 controls the operation of the actuator 108.

Even though the actuator 108 receives an input signal from the actuator control unit 125 so that a uniform pressure is applied to the radial artery 10, the actual applied pressure may decrease with time according to circumstances. When the applied pressure decreases, the baseline of the sphygmus wave declines with time, and the pulse amplitude of the sphygmus wave also tends to decrease. However, even when the baseline of the sphygmus wave is inclined in a decreasing direction, if the pulse amplitude of the sphygmus wave does not decrease, it is determined that the pressure applied to the radial artery 10 is not reduced but the blood pressure of the examinee has actually dropped. Such a difference is used to determine whether to reapply pressure.

Referring to a sphygmus wave WT-A of FIG. 6, a difference between an amplitude BLV1.A of a baseline BL-A of the sphygmus wave WT-A that is measured during a first time t1-A after starting the measuring of continuous blood pressure and an amplitude BLV2.A of the baseline BL-A measured during a second time t2-A that is later than the first time, that is, BLV1.A-BLV2.A, reaches at least a first criterion. The baseline BL-A may be obtained by filtering the sphygmus wave WT-A using a low pass filter. Alternatively, the baseline BL-A may be regarded as a line that is formed by connecting points near to a low peak among two points that divide a section into three parts between a high peak and a low peak of the sphygmus wave WT-A. The low pass filter may be formed in the filter unit 114 (refer to FIG. 2).

The first criterion is difference between the baseline of the pressure pulse at onset of the measurement and the baseline of the pressure pulse measured at some time t. The difference in the baseline may be due to changes in blood pressure, but it the differences in the baseline may also be a result of decreased external pressure applied by the actuator. These differences in the baseline may be used to determine the timing for reapplication of the external pressure as a first indicator. In one embodiment, the first criterion may correspond to a pressure difference of 5 mmHg.

Also, a ratio of a pulse amplitude V1.A of the sphygmus wave WT-A in the first time t1-A to a pulse amplitude V2.A of the sphygmus wave WT-A of the second time t2-A, that is, V2.A/V1.A, is less than or equal to a second criterion. A pulse amplitude (e.g., V1.A and V2.A) is defined as a difference between a high peak and a low peak of a pulse. In one embodiment, the second criterion may be 80%.

When the two conditions are satisfied, that is, when BLV1.A-BLV2.A reaches at least the first criterion and V2.A/V1.A is less than or equal to the second criterion, it is determined that the actual applied pressure of the pressurizing member 107 according to the driving of the actuator 108 decreases as shown by a line PL-A. Accordingly, the repressurizing determining unit 124 determines that pressure is not applied to the radial artery 10 under the second condition and thus pressure needs to be reapplied. As described above, when it is determined that it is necessary to reapply pressure, an operation of reapplying pressure to the radial artery 10 under the second condition is conducted.

Meanwhile, referring to a sphygmus wave WT-B of FIG. 7, a difference between an amplitude BLV1.B of a baseline BL-B of the sphygmus wave WT-B sensed during a first time t1-B after starting the measuring of continuous blood pressure and an amplitude BLV2.B of the baseline BL-B sensed during a second time t2-B that is later than the first time t1-B, that is, BLV1.B-BLV2.B, reaches at least a first criterion. The first criterion may correspond to a pressure difference of 5 mmHg as described above with reference to FIG. 6.

However, the ratio of a pulse amplitude V2.B of the sphygmus wave WT-B of the second time t2-B to a pulse amplitude V1.B of the sphygmus wave WT-B of the first time t1-B, that is, V2.B/V1.B, is greater than a second criterion. The second criterion may be 80% as described with reference to FIG. 6.

In this case, that is, BLV1.B-BLV2.B reaches at least the first criterion but V2.B/V1.B is greater than the second criterion, it is determined that the actual applied pressure of the pressurizing member 107 according to the driving of the actuator 108 is not decreasing. For example, the actual applied pressure may be constant while satisfying the second condition as shown by a line PL-B. Accordingly, the repressurizing determining unit 124 determines that it is not necessary to reapply pressure because pressure is being applied to the radial artery 10 under the second condition. The decrease of the baseline BL-B of the sphygmus wave WT-B is regarded as the actual decrease in the blood pressure of the examinee.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An apparatus for measuring blood pressure comprising:
   a pressurizing unit for applying pressure to a blood vessel of an examinee under a first condition in which the pressure applied to the blood vessel changes or a second condition in which the pressure applied to the blood vessel is constant;
   a pressure sensor for sensing a sphygmus wave and a pressure of the blood vessel under the first condition or the second condition;
   a processor for calculating a systolic standard blood pressure and a diastolic standard blood pressure of the examinee, based on the sphygmus wave and the blood vessel pressure sensed by the pressure sensor under the first condition,
   for calculating continuous blood pressure of the examinee based on the sphygmus wave and the blood vessel pressure sensed by the pressure sensor under the second condition, the systolic standard blood pressure or the diastolic standard blood pressure under the first condition, and a regression equation for calculating tonometric blood pressure, and
   for determining whether pressure applied to the blood vessel during measuring of the continuous blood pressure deviates from the second condition, by
      subtracting, from an amplitude of the sphygmus wave baseline sensed at a first time after starting the measurement of the continuous blood pressure, an amplitude of the sphygmus wave baseline sensed at a second time later than the first time, and
      comparing a ratio of pulse amplitude of the sphygmus wave at the first time to pulse amplitude of the sphygmus wave at the second time to a second criterion,
   wherein when a result of the subtracting reaches at least a first criterion and the ratio is less than or equal to the second criterion, determining that said pressure applied to the blood vessel of the examinee deviates from the second condition during measuring of the continuous blood pressure and, based on the result, using the pressurizing unit to reapply pressure to the blood vessel of the examinee under the second condition during said measuring of the continuous blood pressure; and
   when the result of the subtracting reaches at least the first criterion, and the ratio is greater than the second criterion, determining that pressure applied to the blood vessel of the examinee satisfies the second condition during said measuring of the continuous blood pressure and that the actual blood pressure of the examinee is determined.

2. The apparatus of claim 1, wherein the sphygmus wave baseline is a line that is formed by connecting predetermined points of the sphygmus wave.

3. The apparatus of claim 2, wherein each of the predetermined points is a point between a high peak and a low peak of the sphygmus wave.

4. The apparatus of claim 1, wherein the sphygmus wave baseline is obtained by filtering the sphygmus wave using a low pass filter.

5. The apparatus of claim 1, wherein the first condition is
   an increased pressure condition under which the pressure is increased at a uniform pressure variation rate to apply pressure to the blood vessel, or
   a reduced pressure condition under which pressure applied to the blood vessel is reduced at a uniform pressure variation rate after pressure is applied to the blood vessel to block the blood vessel.

6. The apparatus of claim 1, wherein the second condition is a fixed pressure condition under which a uniform pressure is applied to the blood vessel of the examinee without completely blocking the blood vessel.

7. The apparatus of claim 1, wherein the first criterion is a value corresponding to a pressure difference of 5 mmHg.

8. The apparatus of claim 1, wherein the second criterion is 0.80.

9. The apparatus of claim 1, further comprising an applied pressure determining unit for determining the second condition for measuring continuous blood pressure such that an applied pressure under the second condition is less than the diastolic standard blood pressure.

10. The apparatus of claim 9, wherein a value less than or equal to 80% of the diastolic standard blood pressure is determined as the applied pressure under the second condition.

11. The apparatus of claim 9, wherein the applied pressure under the second condition is less than or equal to a pressure at which an inflection point of an envelope line occurs and wherein the envelope line is formed by connecting high peaks of the sphygmus wave sensed by the pressure sensor under the first condition.

* * * * *